United States Patent [19]

Mericle

[11] Patent Number: 4,971,198
[45] Date of Patent: Nov. 20, 1990

[54] HEMOSTATIC CLIP AND CARTRIDGE ASSEMBLY

[75] Inventor: Robert W. Mericle, Raleigh, N.C.

[73] Assignee: Edward Weck Incorporated, Princeton, N.J.

[21] Appl. No.: 476,116

[22] Filed: Jan. 29, 1990

Related U.S. Application Data

[63] Continuation of Ser. No. 182,652, Apr. 18, 1988, abandoned.

[51] Int. Cl.$^5$ .............................................. B650 85/24
[52] U.S. Cl. ................................... 206/339; 606/158
[58] Field of Search ....................... 606/151, 157, 158; 227/902; 206/338-340; 72/410, 424

[56] References Cited

U.S. PATENT DOCUMENTS

| | | | |
|---|---|---|---|
| 1,830,650 | 11/1931 | Falk | 227/143 |
| 3,363,628 | 1/1968 | Wood | 606/158 |
| 3,713,533 | 1/1973 | Reimels | 606/143 |
| 3,867,944 | 2/1975 | Samuels | 227/DIG. 1 |
| 4,188,953 | 2/1980 | Klieman et al. | 606/158 |
| 4,344,531 | 8/1982 | Giersch | 206/339 |
| 4,696,396 | 9/1987 | Samuels | 606/158 |
| 4,799,481 | 1/1989 | Transue et al. | 606/158 |

*Primary Examiner*—C. Fred Rosenbaum
*Assistant Examiner*—William Lewis
*Attorney, Agent, or Firm*—Robert E. Lee, Jr.

[57] ABSTRACT

A hemostatic clip cartridge for automatically moving a plurality of pre-formed clips to a delivery station of the cartridge while reducing jamming of the clips in the cartridge is disclosed. Jamming is reduced both by using a constant force spring and employing flat surfaces on a portion of opposite sides of the clip located in the plane of the clip. Heart shaped clips having such flat surfaces are also disclosed.

3 Claims, 3 Drawing Sheets

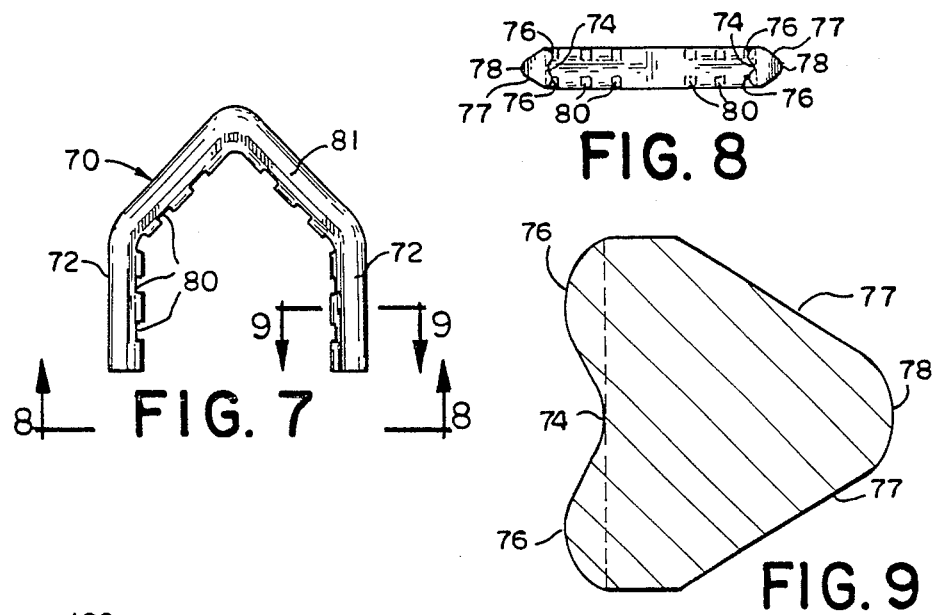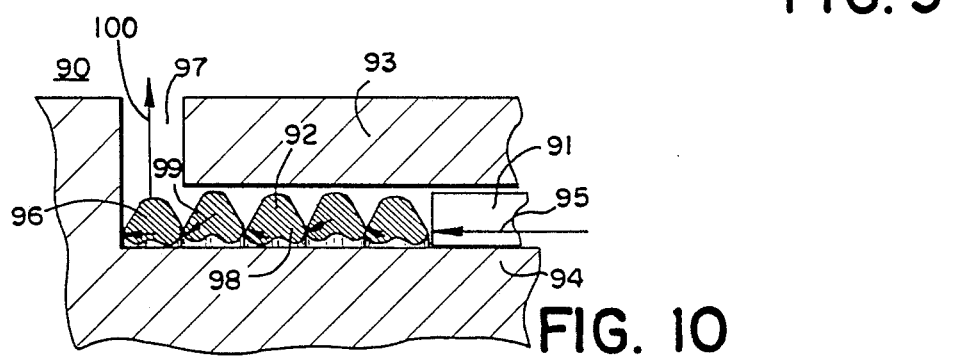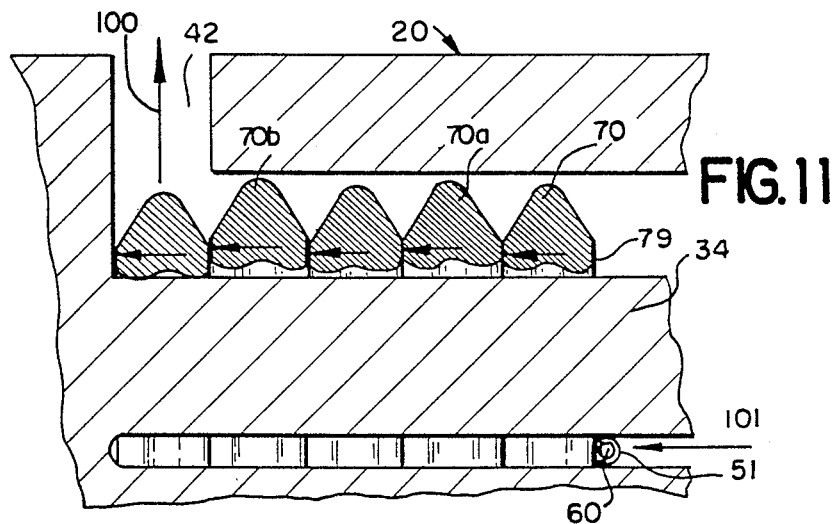

HEMOSTATIC CLIP AND CARTRIDGE ASSEMBLY

This is a continuation of copending application Ser. No. 182,652 filed on Apr. 18, 1988, now abandoned.

BACKGROUND OF THE INVENTION

This invention relates to surgical clips useful for ligating vessels in the human body and to cartridges useful for holding hemostatic clips.

During surgical procedures it is necessary to occlude blood vessels, and while several means are available, the usual method is to clamp such vessels with hemostatic clips. A very successful clip design is described in U.S. Pat. No. 3,363,628 and sold by Edward Weck Incorporated under the trademark HEMOCLIP ®. Such clips are applied with an automatic applier or a hand held forceps-type clip applier which deforms an open clip around the vessel to clamp it shut. In particular, the hand held forceps-type appliers have specially shaped jaws into which individual clips are introduced and then applied to clamp a vessel.

Various packaging means have been used in an effort to supply clips in a manner that is convenient to the surgeon and which involves a minimum of manipulation by the surgeon in picking up a clip in the applier so that it is firmly held until the surgeon has applied it to the particular vessel. Most clips are packaged in some form of cartridge which can be loaded sterilized in a pouch. In general, the cartridges support individual clips in separate compartments. Such cartridges must provide some means of retaining the clips in place until picked up by the clip applier, and these retaining means often present difficulties or inconvenience to the surgeon who is using the clips.

U.S. Pat. No. 4,344,531 discloses a class of hemostatic clip cartridges which automatically move a plurality of pre-formed U shaped or V shaped hemostatic clips, which have been pre-loaded into the clip cartridge, to provide individual hemostatic clips serially at an open delivery station of the cartridge. A surgeon is able to obtain an individual clip in a convenient manner from the same location each time a clip is needed without hindrance from the kind of retaining means associated with compartmented cartridges. In addition, the surgeon is not required to search for a compartment containing a clip, but knows that he can always obtain a clip from the single delivery station of the automatic feed cartridge.

Even these automatic feed cartridges have problems in that clips like those described in U.S. Pat. No. 3,363,628 loaded serially in a row within the cartridge are forced into contact with one another at the curved outer surfaces of the ridges of the clips by a slider and spring arrangement designed to exert a force on the row of clips longitudinally along the cartridge in the direction of the delivery station. Because of the clearances allowed within the cartridges and the curved nature of the contacting surfaces, the clips become misaligned and may jam within the cartridge. Also, when the clips are first loaded into the cartridge a force larger than that which is necessary to move the row of clips is exerted on the clips by the variable force compression spring. This adds to the likelihood that the clips being compressed together will jam. Hence, a new automatic clip cartridge and/or clip design is desired to overcome the aforementioned problem of jamming.

SUMMARY OF THE INVENTION

The clip cartridge of this invention is formed of a base including a rail on which the clips are moved, a cover which retains the clips which are not yet in position to be removed, a delivery station formed by the front end surface of the cover and the inside surface of the front end wall of the base, and means for biasing the clips toward the front end wall of the base with a force which remains constant regardless of the number of clips contained in the cartridge. In the preferred embodiment, the biasing means is a flat coiled spring which is retained at the front end of the base and is adapted to be extended longitudinally along the rail. By providing a constant force spring, the force applied to the clips is minimized to that which is required to move the clips even when the cartridge is full. This helps reduce jamming of the clips.

Another aspect of the invention is to provide clips having two parallel arms connected together at one end. The cross section of the clip comprises a modified triangular cross section with a side facing inwardly and an apex facing outwardly. Each arm includes a flat surface on opposite sides of the clip which are parallel to the plane of the clip.

The clips include a longitudinal valley in the interior surface of the arms facing one another, the depth and width of which is sufficient to form curvilinear ridges alongside. Each flat surface intersects the curvilinear ridge on one side and a triangular side on the other. In the preferred embodiment, the cross section is substantially equilateral and the length of each flat surface is substantially fifteen percent or less of the height of the clip.

BRIEF DESCRIPTION OF THE DRAWINGS

The clip cartridge of the invention will be described in more detail with reference to the accompanying drawings.

FIG. 7 is an elevational view of the clip shown in FIG. 6.

FIG. 8 is a view of the clip taken about line 8—8 of FIG. 7.

FIG. 9 is an enlarged cross sectional view of the clip taken about line 9—9 in FIG. 7.

FIG. 10 is a schematic representation of a prior art automatic cartridge showing the forces at work on the clips.

FIG. 11 is a schematic representation of the automatic cartridge and clips of the present invention showing the forces at work.

DETAILED DESCRIPTION OF THE DRAWINGS

Figure 1:
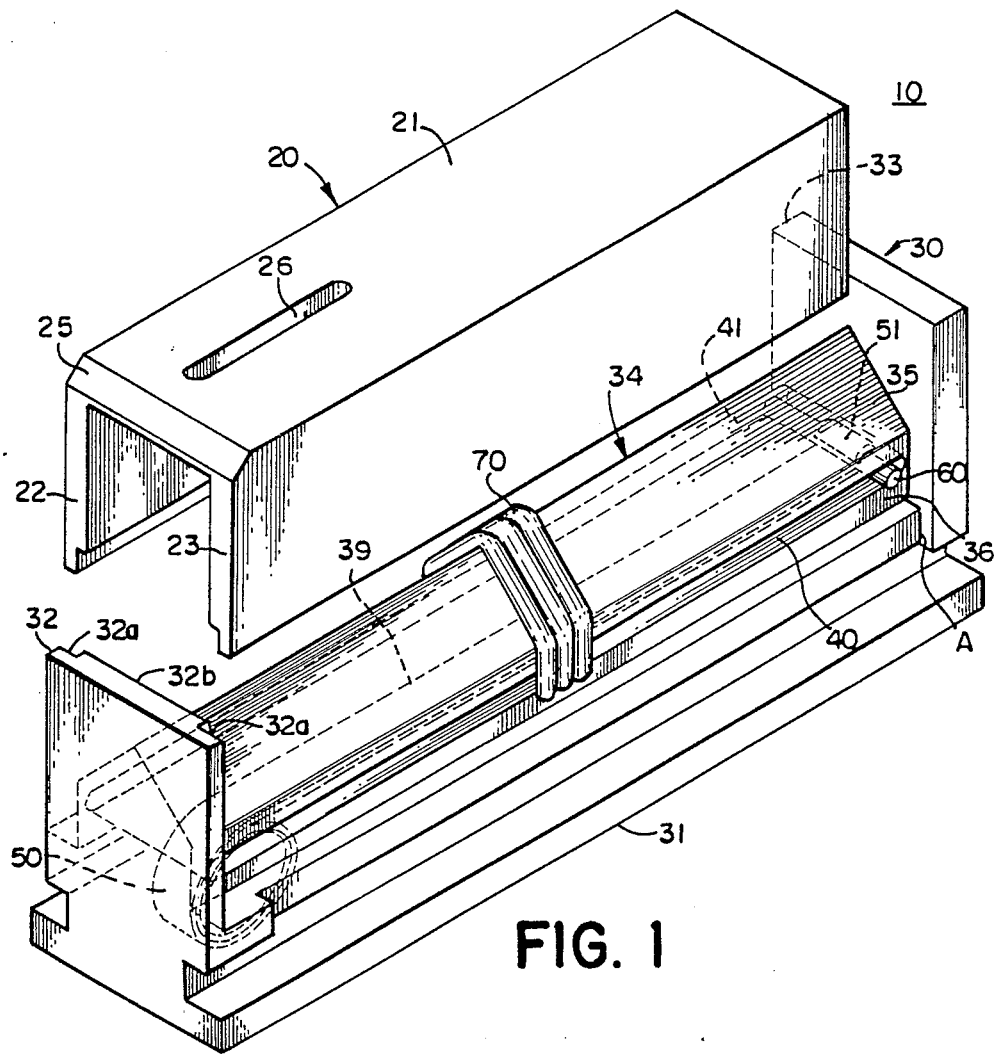
FIG. 1 is an isometric exploded view showing the cover and base of the clip cartridge of the present invention in their relative positions to each other.

In FIG. 1, a specific embodiment of the clip cartridge of the present invention is shown with the individual parts separated but in their relative positions with respect to each other. The assembled cartridge is indicated generally by reference numeral 10 and includes a cover 20, a base 30, a spring 50 and pusher pin 60 as well as a number of hemostatic clips 70.

The base 30 comprises a rectangular pedestal portion 31, which is flat on its underside, and two upstanding, parallel and spaced apart end walls 32 and 33 at either ends of the pedestal 31. The base includes a rail 34 which extends between the end walls 32 and 33 and has a cross section comprising a triangular portion 35 above a rectangular or square portion 36. The rail 34 is sized and shaped to receive a row of hemostatic clips 70 to be described in more detail hereinafter.

Figure 2:
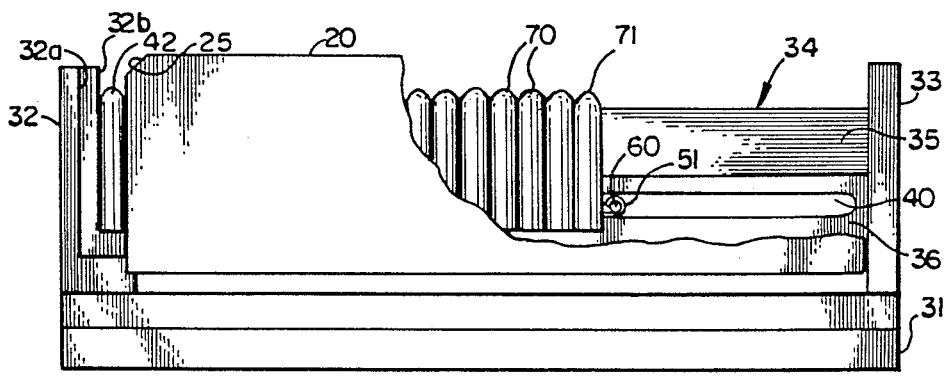
FIG. 2 is an elevational, planar view of the cartridge of the present invention with the cover shown partially broken away.
Figure 3:
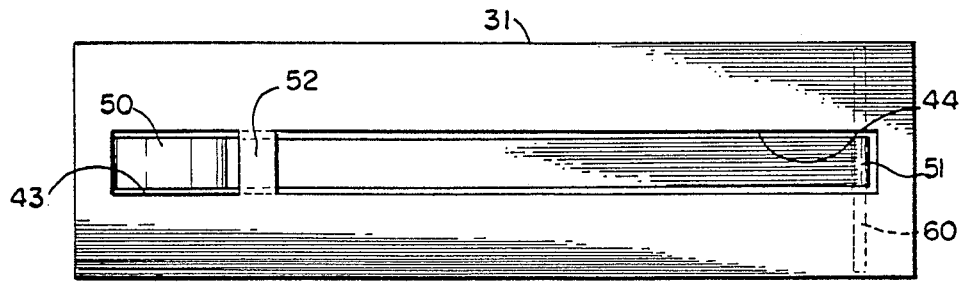
FIG. 3 is a bottom view of the base of the cartridge of FIG. 2.

Referring to FIGS. 1–3, recess 38 is formed in one end of the portion 36 of rail 34 near end wall 32 and communicates with a flat longitudinal slot 39 which runs through the length of the rail to the opposite end wall 33. The slot 39 is as wide as the rail and opens up into elongated apertures 40 and 41 in the side walls of the rail 34. The recess 38 and slot 39 also open up into ambient atmosphere through the opening 43 and elongated opening 44, respectively, in the bottom of the pedestal portion of the base.

The recess 38 is adapted to receive the constant force flat coil spring 50 through the opening 43. A curved first end 51 of the coil is pulled over the coil stop 52 through the longitudinal slot 39 to partially unwind the coil. The remaining coiled portion of the spring 50 is retained the recess 38 against the stop 52. The curved first end 51 forms a cylinder and a pusher pin 60, which is larger than the width of the rail, is inserted through the cylinder. The ends of the pusher pin 60 extend through the elongated apertures 40 and 41 in the sides of the rail.

With a plurality of clips 70 placed on the rail with their spaced apart legs pointed toward the pedestal 31 along the sides of the rail, the protruding portions of the pusher pin 60 are allowed to engage the legs of the end clip 71 which compresses the clips together against the end wall 32 as best seen in FIG. 2. Because the coil spring 50 is a constant force spring, a force greater than that required to move the clips into position at the delivery station 42 is not exerted on the row of clips at initial loading of the clips, where, with a compression spring, the force would be greatest and more than that which is required.

The cover 20 has a flat rectangular top surface 21 and two spaced apart and parallel lengthwise sides 22 and 23 which run from one end of the top surface to the other. The sides are integrally formed with the top in the preferred embodiment. The bottom and ends of the cover 20 are open and the bottoms of the sides 22 and 23 are disposed to engage the base on either side of the rail 34. The inside surfaces of the cover 20 are sized to fit on the base 30 and over rail 34 with sufficient clearance from the rail to permit free passage of the pusher pin 60 and clips 70 but close enough to retain the clips in place no matter to what attitude the clip cartridge assembly 10 may be subjected between assembly and final use. The cover 20 may be formed with any outside surface but is preferably found with flat top and side surfaces.

In order to position properly the cover 20 on the base 30, the cover fits within a recessed area A, and is solvent bonded, welded, or latched in place, for permanent attachment.

Once the cover is in place on the base 30, it extends from the end wall 33 along the rail 34 but does not engage wall 32. The forward end of cover 20 is spaced apart from end wall 32 by a little more than the thickness of a clip 70. This creates the delivery station 42 and allows the jaws of an applier to fit over the clip found in the delivery station 42 and withdraw it from the cartridge.

The cover 20 is preferably found with a chamfer 25 at the top edge of the forward end of the cover 20 to provide easier access by the clip applier jaws to the delivery station 42. The cover 20 is also preferably provided with a slot 26 in the forward part of the top surface of cover 20 to give visual access to the contained clips to make it possible to ascertain the number of clips remaining in the cartridge during use.

Figure 5:
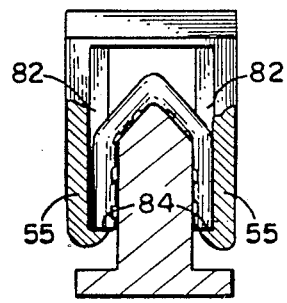
FIG. 5 is an enlarged cross-sectional view illustrating the relative positions of a clip, applicator, and a portion of the cartridge of FIG. 1 during loading of the applicator with a clip from the cartridge.
Figure 6:
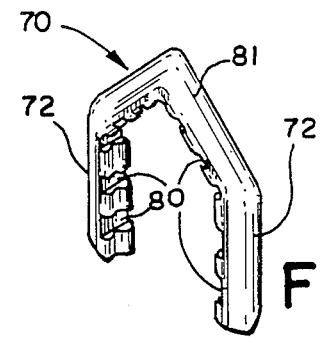
FIG. 6 is a perspective view of a hemostatic clip designed in accordance with the concepts of the present invention.
Figure 4:
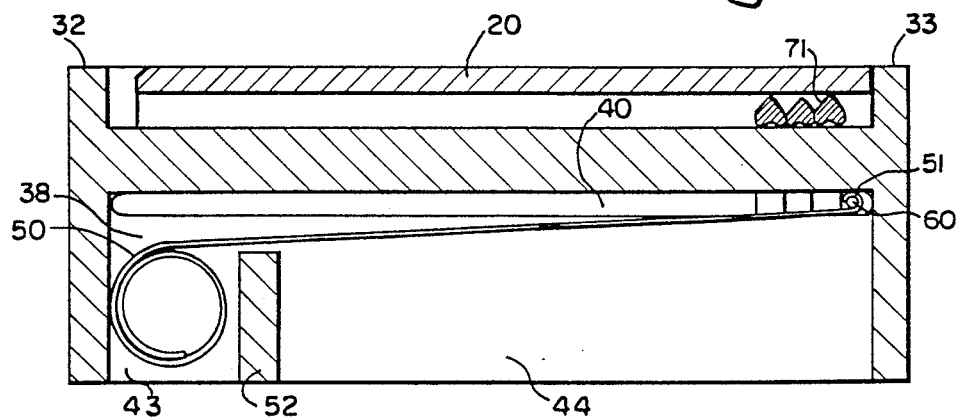
FIG. 4 is an elevational, partial cross section of the cartridge of FIG. 2.

In order to make provision for the added width of the clip applier jaws, shown as 55 in FIG. 5, as compared to the thickness of the clip and prevent the jamming of the jaws in the delivery station, the inside surface of forward end wall 32 is relieved on each side to provide properly spaced bearing surfaces 32a for the jaws and retain a properly positioned support surface 32b for the clip. The clip support surface 32b is closely dimensioned to the ideal inside width of the applier jaws.

Referring now to FIGS. 6 through 9, the hemostatic clip of this invention comprises a modified triangular elongate strip 70 of deformable material, such as stainless steel, tantalum, titanium, etc., having its end portions arranged in parallel and spaced apart arms 72 with the facing inner surfaces of the arms, corresponding to the base of the triangular cross-section, being formed intermediate their lateral edges with a valley or recessed portion 74 extending lengthwise through at least the end portion of the arms and preferably through the entire length thereof. The ridges 76 formed alongside the recessed portion are preferably formed to curvilinear shape. The length and width of the recess is not sufficient to noticeably weaken the clip, yet adequate to leave the ridges that will impress a circumferential band of compression about the blood vessel wherein the clip is attached. Referring in particular to the cross section of the clip in FIG. 9, the triangular sides 77 of the clip form a 60° angle if they were to intersect, but the apex 78 of the triangular cross section is curved. The triangular sides 77 continue until a flat portion 79 of the clip on each side is intercepted. Each flat portion 79 extends from the triangular side 77 to the curvilinear ridge 76 and forms parallel flat surfaces 79 on each side of the clip parallel to the plane of the clip. The distance between the flat surfaces 79 is such as to make the width of the clip between the flat surfaces slightly larger (10% or less) than the height, measured from the apex to a straight line drawn tangential to the top of the ridges 76. The clip could be wider or smaller but this is the preferred width. The inner surfaces of the clip contain a plurality of indentations 80 which are designed to improve clip flatness upon closure and improved vessel gripping clip retention.

In FIGS. 6–9, the arms 72 of the clip are coupled by a U-shaped bail portion 81 which could be formed to other contours, such as V-shaped, rounded or other polygonal shapes.

The provision of the parallel arms 72 and the triangular sides 77 serve to insure a firm gripping action by the applicator. These straight arms 72 of the clip 70 are readily seated in the grooves 82 in the jaws 55, the ridges 84 in the jaws 55 preventing the clip from sliding from the groove 82. Care must be taken however, when grabbing the clip in the delivery station of a cartridge not to squeeze the clip excessively since this will partially close it as the clip is removed. If the applicator has a biased open position, as many do, when the grabbing force is relaxed the jaws will open slightly and the slightly closed clip will fall out of the applicator. With the constant force spring 50 and the flats 79 on the sides of the clips 70, jamming of the clip in the delivery station is reduced and it is less likely that an excessive force will have to be used to remove the clip from the cartridge.

FIG. 10 is a schematic of a cartridge 90 having a compression spring designated 91 and standard, hemostatic, heart shaped clips 92 (with valley 74 and rounded apexes the triangular cross section becomes heart shaped). While the clearance in the Y direction between the cover 93 and the rail 94 in the cartridge is minimized, some clearance is still necessary. Eventhough the force from the spring 91 is only in the X direction as designated by arrow 95, because of the curved sides of the clips where they contact one another, the X directed force is broken into X and Y components which can result in the clip 96 in the delivery station 97 being jammed by its adjacent clip 98 exerting a downward force as denoted by arrow 99. The greater the X directed force 95 from the compression spring 91 the greater the force associated with arrow 99. Force 99 has a downward directed component which resists the force 100 in the plus Y direction exerted by an applicator trying to withdraw the clip 96. As discussed earlier the greater the gripping force by the jaws of the applicator the more the liklihood the clip will be squeezed and fall out of the applicator.

Compare FIG. 10 with the schematic of FIG. 11 in which the X directed force 101 is exerted by a constant force flat coiled spring 50 of FIG. 1 and the clips 70 have flat parallel side surfaces 79 so that no downward Y-directed forces are created to jam the clip even though some of the clips 70a and 70b may be elevated in the gap between the rail 34 and cover 20. Because of the flat surfaces 79 the reaction forces exerted by the clips on one another due to the spring force 101 are all in the X direction. The length of the flat surface 79 along the height of the clip must be large enough to insure overlap of engaging flat surfaces between adjacent clips over the full height of the gap between the rail and cover. The flat surfaces 79 on the clips are not only useful in preventing jamming in the automatic cartridge but also during assembly and handling in loading the cartridges and automatic applicators.

It will be understood that various other changes can be made in the above described cartridge and clip constructions which provide the characteristics of this invention without departing from the spirit thereof, particularly as defined in the following claims.

What is claimed is:

1. A clip cartridge adapted to contain hemostatic clips in serial arrangement comprising a cover, a base including a rail extending between front and rear end walls of said base, said rail shaped to accommodate said clips in serial arrangement thereon and permit said clips to be moved along said rail toward the front end wall of said base; said cover contoured to fit on said base and over said rail to enclose said rail for a major part of rail length in a manner retaining said clips on said rail while permitting said clips to move on said rail, said cover being positioned on said base to provide a delivery station at an unenclosed portion of said rail between an outside surface of the forward end of said cover and the inside surface of the front end wall of said base to permit removal of individual clips from said cartridge by a separate retrieval device; said cartridge further comprising a coiled flat spring for biasing said serially arranged clips toward the front end wall of said base with a force which remains substantially constant regardless of the number of clips contained in the cartridge, said coiled spring being retained at the front end of said base and adapted to be extended at one end longitudinally within said rail to the opposite end of said base, said cartridge comprising a pusher pin connected to said one end of said coiled spring and adapted to engage the end clip most remote from said delivery station, said pusher pin extending substantially perpendicularly to said extended spring through elongated slots in either side of said rail to engage said end clip.

2. A clip cartridge comprising a plurality of clips in column arrangement, each clip comprising a pair of arms interconnected at one end and opened at the other with the arms arranged in laterally spaced apart substantially parallel relation, each of said arms having a modified triangular cross-section, with a side facing inwardly and with an apex facing outwardly, at least one longitudinal valley in the inwardly facing sides of said arms, and a flat surface on opposite sides of said clip parallel to the plane of the clip, said flat surfaces intersecting sides of said clip extending outwardly from one another from said apex, the flat surfaces of said clips opposing one another in said column arrangement, a base including a rail extending between front and rear end walls of said base, said rail shaped to accommodate said clips in serial arrangement therein and permit said clips to be moved along said rail toward the front end wall of said base; means coupled to said base for retaining said clips on said rail while permitting said clips to move on said rail; a delivery station to permit removal of individual clips from said cartridge by a separate retrieval device; said cartridge further comprising a coiled flat spring for biasing said column of clips toward the front end wall of said base with a force which remains substantially constant regardless of the number of clips contained in the cartridge, said coiled spring being retained at the front end of said base and adapted to be extended at one end longitudinally along said rail to the opposite end of said base, said coiled spring further comprising a pusher pin connected to said one end thereof and adapted to engage the end clip most remote from said delivery station.

3. The clip cartridge of claim 2 wherein said coiled spring is extended longitudinally within said rail and said pusher pin extends substantially perpendicularly to said extended spring through elongated slots on either side of said rail to engage said end clip.

* * * * *